US010278733B2

(12) United States Patent
Walker et al.

(10) Patent No.: US 10,278,733 B2
(45) Date of Patent: May 7, 2019

(54) TATTOO ENHANCEMENT PROCEDURE

(71) Applicant: ALTAIR INSTRUMENTS, INC., Ventura, CA (US)

(72) Inventors: Douglas W. Walker, Ventura, CA (US); Brenda A. Acosta, Ventura, CA (US); John Hubble, San Diego, CA (US)

(73) Assignee: Altair Instruments, Inc., Ventura, CA (US)

( * ) Notice: Subject to any disclaimer, the term of this patent is extended or adjusted under 35 U.S.C. 154(b) by 477 days.

(21) Appl. No.: 15/085,915

(22) Filed: Mar. 30, 2016

(65) Prior Publication Data

US 2016/0287288 A1 Oct. 6, 2016

Related U.S. Application Data

(60) Provisional application No. 62/141,709, filed on Apr. 1, 2015.

(51) Int. Cl.
*A61B 17/54* (2006.01)
*A61K 8/31* (2006.01)
(Continued)

(52) U.S. Cl.
CPC ............ *A61B 17/54* (2013.01); *A61K 8/31* (2013.01); *A61K 8/37* (2013.01); *A61K 8/42* (2013.01); *A61K 8/678* (2013.01); *A61K 8/891* (2013.01); *A61K 8/922* (2013.01); *A61Q 19/00* (2013.01); *A61B 2017/00747* (2013.01); *A61B 2017/306* (2013.01); *A61B 2217/005* (2013.01)

(58) Field of Classification Search
CPC ............... A61B 17/54; A61B 17/545; A61B 2017/00747; A61B 2017/00761; A61B 2017/00769
See application file for complete search history.

(56) References Cited

U.S. PATENT DOCUMENTS

| 2,712,823 A | 7/1955 | Kurtin |
| 2,867,214 A | 1/1959 | Wilson |

(Continued)

FOREIGN PATENT DOCUMENTS

WO    WO2011-087852    7/2011

OTHER PUBLICATIONS

International Search Report and Written Opinion dated Jul. 6, 2016 in International Application No. PCT/US2016/025340.

*Primary Examiner* — Ashley L Fishback
(74) *Attorney, Agent, or Firm* — M. J. Ram and Associates; Michael J. Ram (57) ABSTRACT

A method is described for brightening tattoos or pigmented images formed below the epidermis of an individual. A skin treating device having a treatment tip with a crystalline abrasive material permanently bonded thereto is moved across the skin surface covering the tattoo. The procedure results in the bonded crystalline abrasive material removing a portion of the surface of the epidermis of the skin area over said tattoos or pigmented images, resulting in a brightening of colored or black line tattoos and a sharpening of the lines in the image. Simultaneously applying a vacuum to the skin surface during the procedure and the application of skin serum during or after the procedure enhances the results.

7 Claims, 6 Drawing Sheets

(51) Int. Cl.

| | | |
|---|---|---|
| *A61K 8/37* | (2006.01) | |
| *A61K 8/42* | (2006.01) | |
| *A61K 8/67* | (2006.01) | |
| *A61K 8/891* | (2006.01) | |
| *A61K 8/92* | (2006.01) | |
| *A61Q 19/00* | (2006.01) | |
| A61B 17/00 | (2006.01) | |
| A61B 17/30 | (2006.01) | |

(56) References Cited

U.S. PATENT DOCUMENTS

| | | |
|---|---|---|
| 2,881,763 A | 4/1959 | Robbins |
| 2,921,585 A | 1/1960 | Schumann |
| 3,964,212 A | 6/1976 | Kårdén |
| 4,378,804 A | 4/1983 | Cortese, Jr. |
| 5,012,797 A | 5/1991 | Liang et al. |
| 5,037,431 A | 8/1991 | Summers |
| 5,800,446 A | 9/1998 | Banuchi |
| 6,241,739 B1 | 6/2001 | Waldron |
| 6,423,078 B1 | 7/2002 | Bays |
| 6,500,183 B1 | 12/2002 | Waldron |
| RE42,960 E | 11/2011 | Waldron |
| 8,221,437 B2 | 7/2012 | Waldron et al. |
| 2001/0023351 A1 | 9/2001 | Eilers |
| 2003/0212415 A1* | 11/2003 | Karasiuk ................ A61B 17/54 |
| | | 606/131 |

* cited by examiner

TATTOO ENHANCEMENT PROCEDURE

This application claims benefit of U.S. Provisional Application 62/141,709 filed Apr. 1, 2015.

A process in which the appearance of Tattoos, body art and injected ink is improved is described below. This process uses Microdermabrasion, or skin resurfacing and rejuvenation to improve the clarity, definition and color brightness of existing tattoos. This microdermabrasion technique, or method, may be used with or without skin serums or lotions.

BACKGROUND

Use of abrasion techniques can be traced back to the ancient Egyptians who used alabaster and pumice to remove blemishes and rough spots and to make the skin smooth and soft. Subsequent thereto, abrasive tipped devices or rotating brushes and cylinders coated with abrasive particles, such as diamond dust, have been used to remove multiple skin layers (U.S. Pat. Nos. 2,712,823; 2,867,214; 2,881,763; 2,921, 585). U.S. Pat. No. 5,800,446 describes a stick, glove finger tip or glove palm coated with an abrasive material which is rubbed over the skin surface to provide a polishing action. U.S. Pat. No. 3,964,212 directed to a pneumatic grinding machine for flat surfaces, incorporates a rotating grinding tool enclosed in a housing with air flowing over the surface to collect dust created by the grinding operation. U.S. Pat. No. 4,378,804 is directed to a skin abrasion device which uses flowing water to rotate an abrasive brush and create a vacuum to remove loosened skin particles. The rotating brush is usually used in conjunction with a liquid detergent or medicinal compound applied to the skin surface being scrubbed. Chemicals, ultrasonic oscillating tips (U.S. Pat. No. 5,012,797) and lasers have also been used for a more aggressive abrasion. U.S. Pat. No. 5,037,431 describes the use of a pressurized jet of a liquid, such as water or sterile saline, to fragment and remove diseased tissue without harming surrounding healthy tissue. This device operates in conjunction with vacuum aspiration to remove the liquid and fragmented tissue.

Microdermabrasion is term which has been adopted to refer to a process where an abrasive material is applied to skin surfaces for removing portions of the epidermis, particularly the top layer of cells of the epidermis, referred to as the Stratum Corneum. Some manufacturers of microdermabrasion device have also referred to the same procedure as "macro exfoliation". This is preferably accomplished with a wand having crystals, particularly diamond particle, permanently attached to the tip of a hollow tube brought into contact with the skin surface. An opening extending through the center of the tube is preferably attached to a vacuum source to increase contact of the abrasive tip with the skin surface and to collect cells and other material removed from the skin surface. This crystal coated treatment tip, also referred to as a wand, removes the top layer of skin through an abrasive process such as disclosed in the Waldron U.S. Pat. No. 8,221,437 entitled Device For Applying Liquid Skincare Products In Combination With Vacuum And Abrasion, RE42,960 and U.S. Pat. No. 6,500,183 entitled Microdermabrasion Device and U.S. Pat. No. 6,241,739 entitled Microdermabrasion Device And Method Of Treating The Skin Surface, said patents incorporated in their entirety by reference herein.

Figure 1:
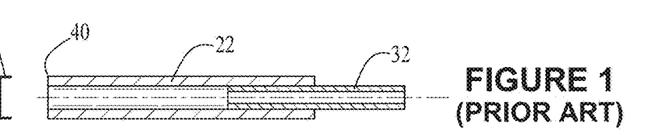
FIGS. 1 and 3 are cutaway side views of two different treatment tubes usable for performing microdermabrasion.
Figure 2:
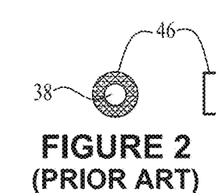
FIGS. 2 and 4 are end views of the two different treatment tubes of FIGS. 1 and 3, respectively.
Figure 3:
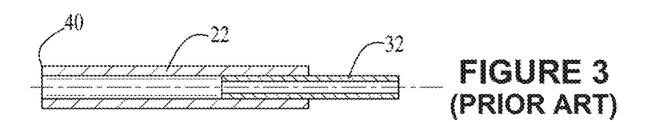
Figure 4:
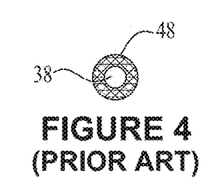

FIGS. 2 and 4 show removable discs 46, 48 sized to fit over the end 40 of the tube 22 shown in FIGS. 1 and 3. The discs 46, 48 have an abrasive end or abrasive material attached to the outer end. During the microdermabrasion procedure various discs with different abrasive characteristics can be interchanged and at the conclusion of the procedure the disc(s) 46, 48 can be discarded.

Figure 5:
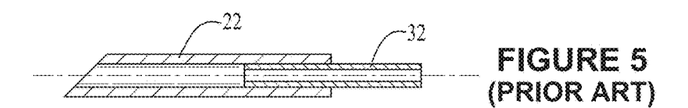
FIG. 5 is a cutaway side view of the end of a sloped treatment tube.
Figure 6:
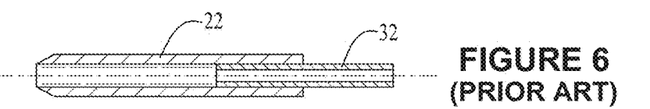
FIG. 6 is a cutaway side view of the end of a tapered treatment tube.
Figure 7:
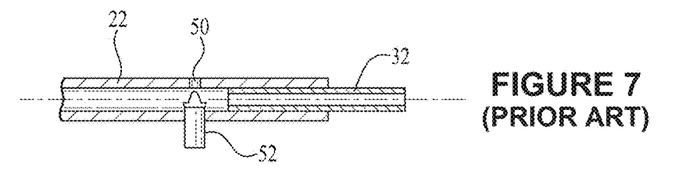
FIG. 7 is a cutaway side view of a valved treatment tube.
Figure 8:
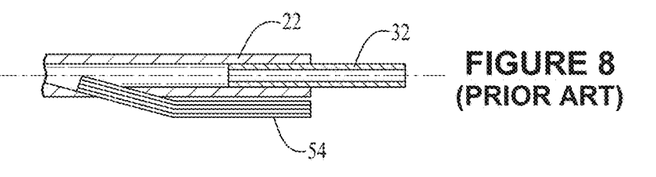
FIG. 8 is a cutaway side view of the end of a treatment tube with a second tube for delivery of a supplemental treatment fluid.

Besides providing different means of abrasion on the end of the treatment tip 22, the contour or shape of the tip can be varied. FIGS. 1 and 3 show a flat end. The flat end can provide a greater surface area in contact with the skin for an aggressive removal of surface cells. For easier access to difficult to reach locations the abrasive tips can be sloped, as shown in FIG. 5, or tapered, rounded, cone shaped or concave, as shown in FIG. 6-8, to better treat curved surfaces, such as the area between the cheek and the nose.

The device is attached to a vacuum pump (not shown) through tube 32, the pump generating a constant level of vacuum, which is controlled (lessened) by the venting of air into the system using a valving mechanism. (not shown). As an alternative, the full vacuum can be applied to the tube or wand assembly 22. The level of vacuum can then be decreased by air vented into the system through vent hole 50 by adjusting flow control valve 52 mounted on the wand or treatment tube 22, as shown in FIG. 7. The valve 52 can be configured to be a simple on/off control or variable so that suction can be readily adjusted by the operator while performing the procedure. A further embodiment includes a vacuum pump mounted on or adjacent to the tube.

While the treatment tube can be used alone to abrade the skin and the vacuum system can be configured to primarily pick up the loosened skin cells, applying the vacuum through the hole 38 in the end of the treatment tip 46, as described in the Waldron patents provides an unexpected advantage. The skin being treated is pulled against the abrasive tip, thus increasing the effectiveness of the tissue abrasion and removal process. Sealing off ambient air raises the level of vacuum and makes the abrasion more aggressive. A concave tip is particularly effective when used in conjunction with a vacuum, as it provides a larger surface area for the skin/abrasive material contact.

Figure 9:
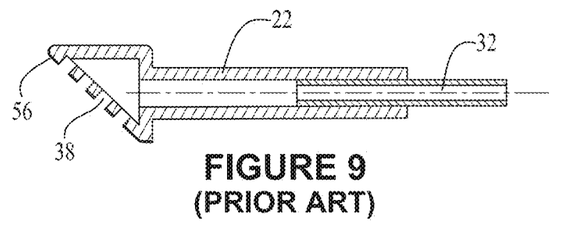
FIG. 9 is a side cutaway side view of the end of a treatment tube with an enlarged, sloped end.
Figure 10:
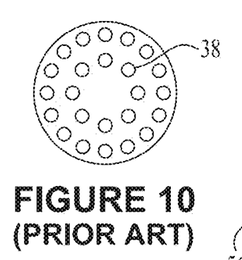
FIG. 10 is an end view of the treatment tube of FIG. 9.
Figure 11:
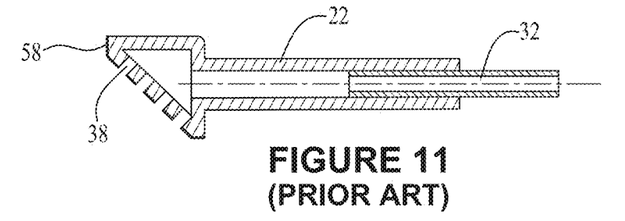
FIG. 11 is a side cutaway side view of the end of a treatment tube with an enlarged, sloped concave end.
Figure 12:
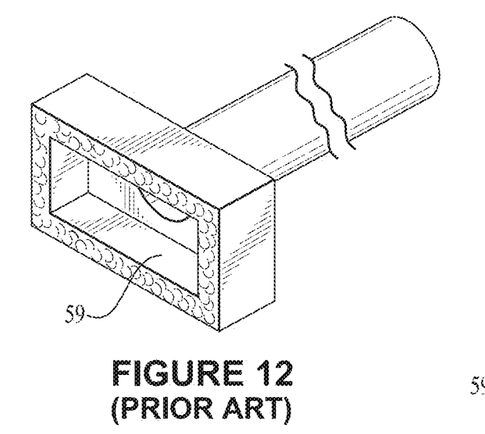
FIG. 12 is a view of a rectangular shaped treatment surface with the handle being the conduit for the vacuum.
Figure 13:
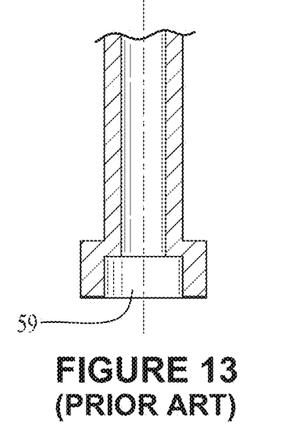
FIG. 13 is a cutaway side view of the end of the treatment tube with an enlarged, rectangular shaped end shown in FIG. 12.

As a further variation, the treatment tip 22 can have an enlarged abrasive coated end 58 which is flat and slopped or sloped and concave such as shown in FIGS. 9 and 10 respectively. While a single hole 38 in the center of the end 56, 58, 59 may be used for applying the vacuum, the efficacy of the abrasive tip can be improved by using several holes 38 therein. FIG. 10 is an end view showing an example of a flat, sloped abrasive tip with multiple openings for application of the vacuum to the skin surface. Further, while FIGS. 5-11 show the end to be part of the treatment tip 22 it could be a separate removable piece as shown in FIGS. 1-4. These configurations have particular utility in treating large flat body surfaces such as the chest, back and legs of an individual. They can also be used where a large abrasive treatment surface is desired but it is preferential to spread out the applied vacuum so that it does not aggressively suck skin into the tip or suck the skin into the tip at a single point.

FIG. 8 shows a second tube 54 mounted on the treatment tip 22. The tube can be used to allow the metered use of chemicals or serum to enhance the abrasion, supply other liquids to reduce friction or materials to enhance the healing or appearance of the treated surface.

Figure 14:
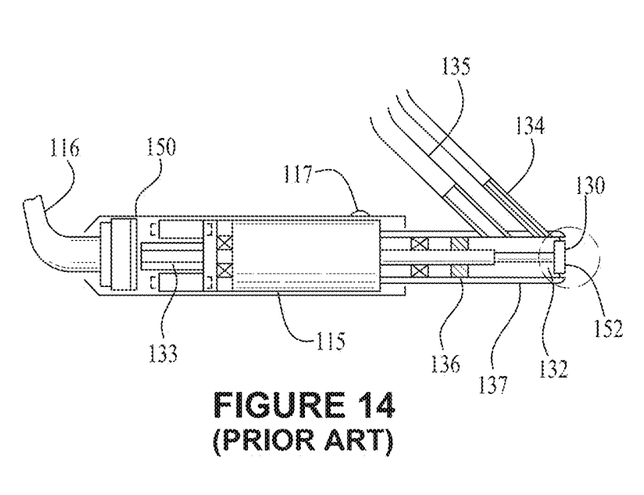
FIG. 14 is cutaway side view of a hand piece with a rotating abrasive tip which is used in a manner similar to the devices shown in FIGS. 1-13.

FIG. 14 shows a hand piece 150 with a rotatable abrasive tip within the tube comprising a rotating abrader assembly 132, 152 which is removable for cleaning. An abrasive coating 130 on the working end of the rotating abrader 132 is used to abrade the skin surface. Rotation of the abrader 132 is provided by electric motor 133 which is activated by the on/off control 117 mounted on the hand piece. An alternative is to use a foot pedal (not shown) to turn the motor on and off. Tubing 134 provides fluid for irrigation in prior applications, or in the presently claimed method for delivery of the serum. Tubing 135 is a conduit for providing a vacuum force to the abrasion site, the opposite end being connected to the particle collection system (not shown) and vacuum source (not shown). The vacuum is maintained in the hand piece 150 tip by vacuum seal 136. This seal also keeps fluids out of the motor portion of the hand piece. The components of the hand piece are enclosed within housing 137; the open end 152 provides contact with the skin and creates a chamber for the vacuum. The housing 137 may be constructed of a clear plastic for visibility, structural plastics or any of numerous metals, such as stainless steel or aluminum, frequently used for medical instruments and which can be easily cleaned and sterilized.

Figure 15:
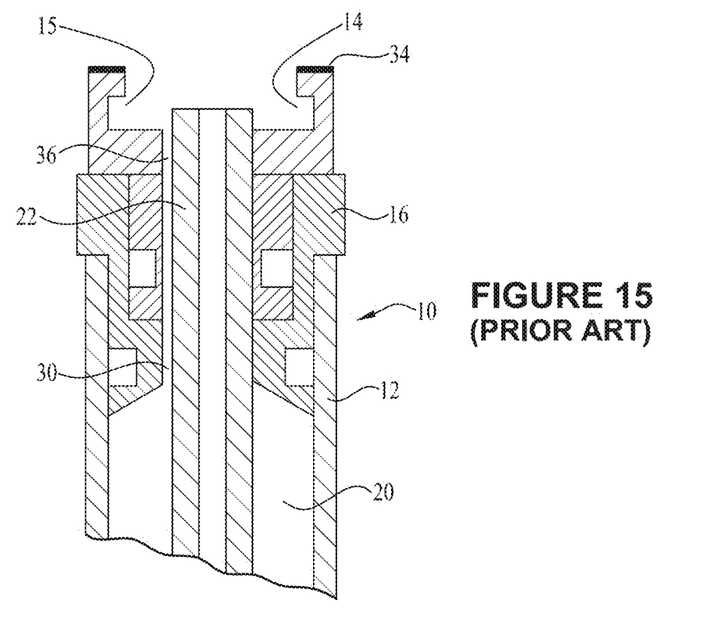
FIG. 15 is a cross section view of another version of a microdermabrasion device with a liquid applicator.
Figure 16:
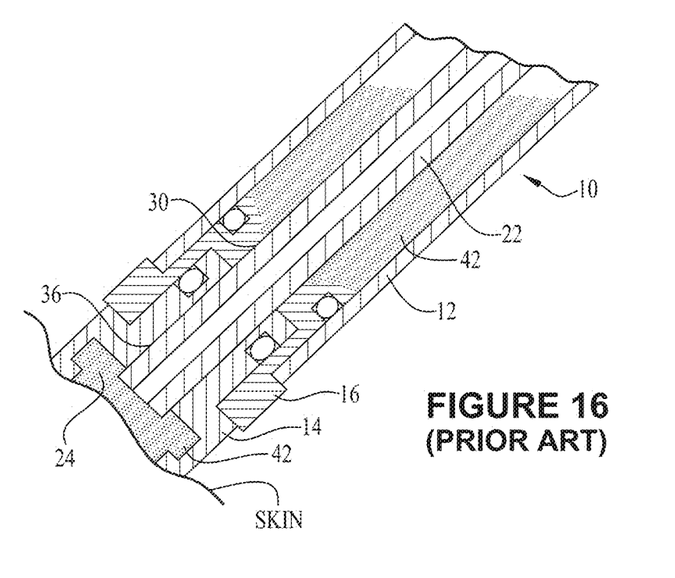
FIG. 16 is an assembled longitudinal cross sectional view of the applicator of FIG. 15 applied to a skin surface during a microdermabrasion procedure with fluid deliver.

FIGS. 15 and 16 are cross sectional views of another version of a microdermabrasion wand 10. The wand 10 comprises a tubular cylinder 12 having, a front seal 16, a wand tip 14 rotationally mounted within the front seal 16. A rear seal (not shown) on the opposite end of the cylinder 12 forms an enclosed space 20 between the front seal 16 and the rear seal. The distal surface of the wand tip has an abrasive surface 34, preferably formed by diamond crystals permanently bonded thereto such as shown in the prior U.S. Pat. Nos. 6,241,739 and 6,500,135, said patents incorporated herein, in their entirety, by reference. Alternatively, the wand tip can be coated with other abrasive substances. A vacuum tube 22 has a distal end within a hole longitudinally through the center of the wand tip 14 and into a pad chamber 15 in the wand tip 14 and extends distally into the pad chamber 15 through the front seal 16, the enclosed space 20, and through the rear seal with a proximal end extending outward for attachment to a vacuum source (not shown). The outer diameter of the vacuum tube at the point where it passes through the front seal and the wand tip is just slightly smaller than the inner diameter of those two components so that flow of fluid held within the enclosed space 20 is substantially restricted but for the grooves 30 and 36. A filter pad 24 is located within the wand tip 14. Preferably the filter pad 24 has a central hole 32 which coincides with the distal end of the vacuum tube 22. In use, the fluid in the delivery wand 10 passes into the pad chamber 15, the pad 24 and onto the skin surface being treated. Each of the front seal 16, rear seal 18 and wand tip 14 have O-ring seals 25, or similar sealing devices, to form a liquid tight seal with the component which is around it. For example, an O-ring seal 25 is located between the front seal 16 and the rear seal in the first instance and the cylinder 12 as well as between the wand tip 14 and the front seal 16. The cylinder 12, wand tip 14, front seal 16 and rear seal 18 are reusable while the filter pad 24 is a single use disposable. The parts can be disassembled for cleaning between treatments.

FIG. 16 shows the fluid path from the enclosed space 20, along the aligned grooves 30, 36 in a flow orientation and into the filter pad 24. Even though a vacuum is applied to the vacuum tube 22, the fluid is not drawn up the vacuum tube 22 because the end is sealed against the skin and no air can flow through the tube. When the hand piece is removed from the skin air flows passed the tip and through the vacuum tube but the majority of fluid is still captured in the filter pad and remains in the enclosed space 20 because no vacuum is applied to the fluid therein.

Vacuum pressure also affects the flow rate of the fluid. A reasonable setting for fluids with the viscosity similar to water is between 1 and 8 in-hg negative pressure. For viscous fluids a vacuum setting of about 10 in-hg gives a proper flow. However, one skilled in the art will recognize that these are only suggested settings and a variety of settings can be used.

To use a microdermabrasion device, the vacuum may be applied, through the treatment tool, to the area of the skin to be treated while the abrasive surface is moved over the skin surface to be treated. The abrasive tip is typically moved over the skin surface in a circular motion. However, a combination of vertical and horizontal movements of the tip, with or without the circular movements, may also be used to assure that the skin area is uniformly treated. The prior art has taught that if a particular skin blemish or abnormality is to be removed from the skin the tip motion can be restricted to that particular portion of the skin.

However the process described herein below is not limited to use of the devices described above and in the Waldron patents and said tattoo brightening can be practiced by using various later patented devices which utilize abrasive coated devices. In addition, an alternative procedure is the use of circulating aluminum oxide, sodium chloride, or sodium bicarbonate crystal or other abrasive materials. These procedures, and particularly the use of crystals permanent attached to a device surface, are proven to be medically safe and effective

BRIEF DESCRIPTION OF DRAWINGS

FIGS. 1-16 illustrate prior art devices shown in the above referenced prior issued Waldron patents, said devices being suitable for use in the new and unique process described herein below for tattoo enhancement.

DETAILED DESCRIPTION

The biological and medical benefits of microdermabrasion also referred to as "macro exfoliation" are well-known and documented. Prior uses of the process have been primarily for anti-aging, anti-wrinkle, or medical ailment treatment purposes. Individuals skilled in the art have believed that micro-dermabrasion could remove tattoos because it was removing one or more layers of skin. However, no evidence exists to demonstrate this possible use. Contrary to that belief, microdermabrasion cannot be used to remove tattoos and applicants have unexpectedly discovered that this was not true. During a clinical evaluation study carried out by the applicants to determine the effects of microdermabrasion on tattoos, it was found that the opposite occurred; the process did not remove tattoos and in fact was found to enhance and brighten the tattoos because the pigments used to form the tattoos are too deeply embedded under the skin surface (i.e., below the epidermis). An unexpected result of this study was that the definition, clarity and brightness of tattoos was perceivable improved. It was determined that this appears to be due to the rejuvenating and resurfacing results of microdermabrasion. It has been medically documented that microdermabrasion works by resurfacing and rejuvenating the skin. This is accomplished by re-texturing the skin surface to improve the cells on a cellular level as well as stimulating collagen production. It also improves the hydration or water content of the skin. Further, it reduces Hyper-pigmentation, Dyschromia, Acne, Rhytoids and scarring and improves skin texture and evens skin tone. It has now been discovered that these properties improve the light transmissive effects of skin and thus improve the clarity, definition, color and brightness of tattoos and body art. It was also found that these results can be further enhanced with the use of skin serums. Furthermore, this process was found to be effective on different skin surfaces (arm, leg, body, face) and all types of tattoos (black and white, gray, colored, geometric, realistic and hyper realistic and Asian). It was also found to be effectively enhance tattoos on all shades of skin as well as individuals of different ethnicities.

In one embodiment, the tattoo brightening process was carried out with diamond-tipped wands with grit sizes of between 100 mm-850 mm. The diamond particles were attached to the wand using a common diamond bonding process known in the art. A preferred size for the crystals bonded to the tip surface is a roughness of 420-650 microns. In a preferred embodiment the device used had diamond particles attached to a stainless steel tube (17-4 PH); however, a tube of any metal, plastic, polymer resin or other hard surface can be used in place of stainless steel. Body contour wand sizes of ½ inch, ¾ inch, and 1 inch diameter, and rectangular tube ends about 1¼ inch width were used, as well as ½ circular wand tips which worked well for small, and hard to reach tattoos. However, the tattoo brightening procedure can be performed with a broad range of abrasive tip sizes and any surface provided with abrading qualities, as long as the abrasion does not go beyond the epidermis. Preferably a vacuum is also used. Further, an abrasive surface with a fluid or particle removal system can be used to remove the top layer of the epidermis in a safe and well-tolerated manner. Examples of suitable vacuum systems are disclosed in the above referenced micro-dermabrasion patents issued to Waldron, incorporated herein by reference.

It was found that an integral hand-held unit with all operable components contained therein worked best. This was due to the inherent mobility, size, and ergonomics of such devices. A 1.2 pound handheld unit with speed (vacuum pressure) control, powered by an internal 9 volt battery and an internally mounted vacuum pump worked most efficiently. However, the prior art devices described above are also suitable for the tattoo brightening method described herein.

Alternative embodiment include a guide for the user regarding manually or automatically setting the unit controls to maximize the tattoo brightening based on the size, coloring, and pattern or type of tattoo. Adjustments to optimize operation for different skin type can also be utilized. Such adjustments can take the form of a setting in the device or the use of different abrasive coated tips to program the best operational parameters, or settings desired, for the intended us. These can be a customized settings which program the operational variables of the microdermabrasion device, such as a preset program that can vary the vacuum pressure or other settings based on the type of tattoo to be treated or the skin characteristics covering the tattoo.

Also, a liquid, referred to as a serum or lotion, can be applied to the skin surface, prior to, during or after the microdermabrasion or macro exfoliation process, the type or amount of serum used being selected based on the tattoo and/or skin characteristics. The serum is generally applied immediately after the microdermabrading treatment. This allows the ingredients comprising the serum to most readily work and function. The serum also aids in rejuvenating, retexturing, and moisturizing the skin. The serum also supplies the tissue directly with vital minerals, vitamins and compounds to improve skin tone, function, and appearance, the skin growth and revitalization being enhanced by the use of the serum.

The microdermabrasion procedure enhances and improves the appearance of tattoos and body art is as a result of the subsequent growth of new, younger skin. The light transmissive properties of the skin are also improved with serum as the skin becomes less opaque. Suitable active ingredients or compounds in the serum include, but are not limited to Isododecane, Phenyl Trimethicone, Isostearyl Palmitate, Diethicone, oxidized corn oil, Tocopheryl Acetate (vitamin E), Glycine Soja (soybean) seed extract, Ceramides (Sphigolipids), Cyclocopentasiloxane, Dimethiconol, C12-15, Alkyl Benozoate, Olea Europea, Fruit Oil, Fragrance, Argania Spinosa Kernal Oil, Helanthus Annuus (Sunflower) Seed Oil, Passiflora Edulis Seed Oil, Copaifera Officinals (Balsam Copaiba) Resin, Chloroxylenol, Avobenzone, Octinoxate, Octisalate, Octorcrylene, Oxybenzone, Paraffin, Tocopherol, Mineral Oil, Lanolin, Dimethicone, and Beeswax. Different compounds or ingredients may work better for different types of body art or skin surfaces, and different serums can be fabricated for different types of tattoos, body art, skin types and treatments.

A further alternative is to use an abrasive tipped wand, that includes a liquid or serum delivery capability such as shown in U.S. Pat. No. 6,500,183 or 8,221,437 to Waldron, incorporated herein in their entirety by reference. The flow rate for delivery of the serum through the wand is adjustable using control mechanisms included in the wand construction. A dry or wet microdermabrasion procedure, or some combination thereof, can be performed. As with typical microdermabrasion the wand or handpiece tube head is used to abrade the top skin layer. Crystals or diamond coatings are most effective. The wand or hand piece tube head delivers the serum or lotion which is administered to the skin area by the operator. This has the immediate benefit of improving the tattoo or body art by improving definition, clarity, color, and brightness.

Example 1

A typical procedure using the process described herein is as follows:

The skin surface to be treated is cleaned using a soap solution to remove oil, make-up and surface dirt. The appropriate diamond coated tip is attached to a hand piece which includes an internal vacuum generating source. The treatment tool is provided with two treatment tips with diamond crystals permanently attached thereto:

Fine: 200/230 Mesh (63/75 Microns) for first time users and for treating delicate areas Medium: 140/170 Mesh (90/107 Microns) used for subsequent treatments or less delicate areas After activating the vacuum pump the crystal containing tip is placed in contact with the skin surface and continuously moved across the skin over the tattoo in a crisscrossing or circular motion until the entire skin covering surface has been treated. A typical process for a tattoo such as shown in FIGS. 17 and 18 is painless, feels like a massage of the area and takes about 10 minutes.

A liquid skin serum can then be rubbed into the treated area to further enhance the appearance of the brightened tattoo. A preferred serum comprises a mixture of Isododecane, Phenyl Timethicone, Isotearly Palmitate, Dimethicone, Oixdized cor oil, Vitamin E, Ceramides. A sunscreen can also then be applied to the treated area.

Figure 17:
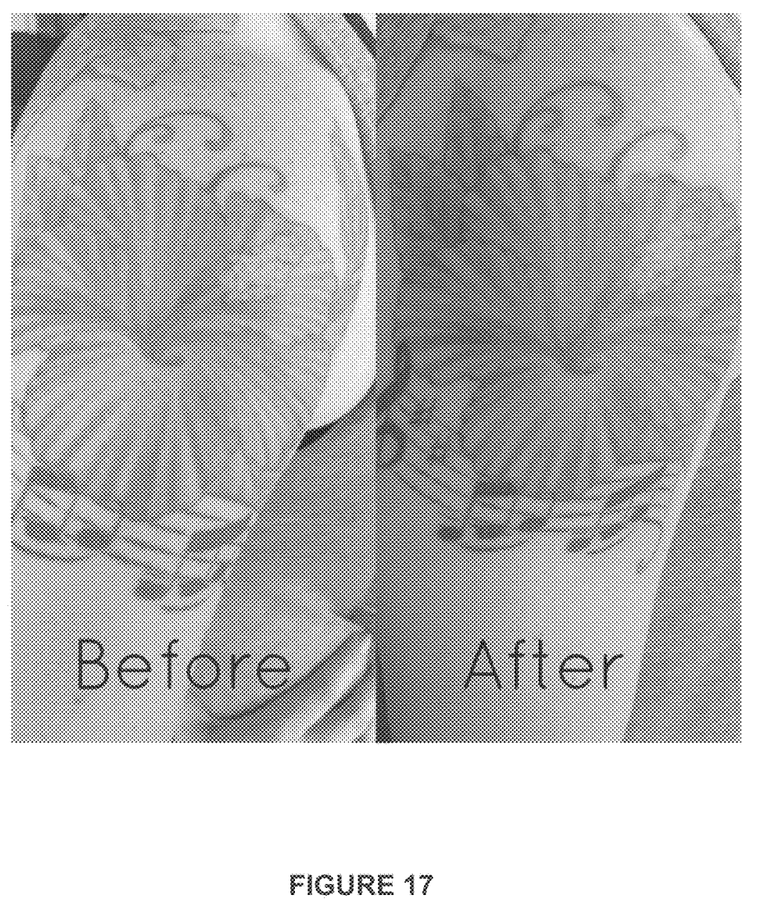
FIG. 17 is a first photograph showing colored images of a tattoo before and after use of the tattoo brightening procedure described herein.

FIG. 17 shows a first tattoo before (left image) and after (right image) application of the above procedure. In the before image the tattoo appears dull and faded; in the after image the lines are sharpened and the colors are brighter.

Figure 18:
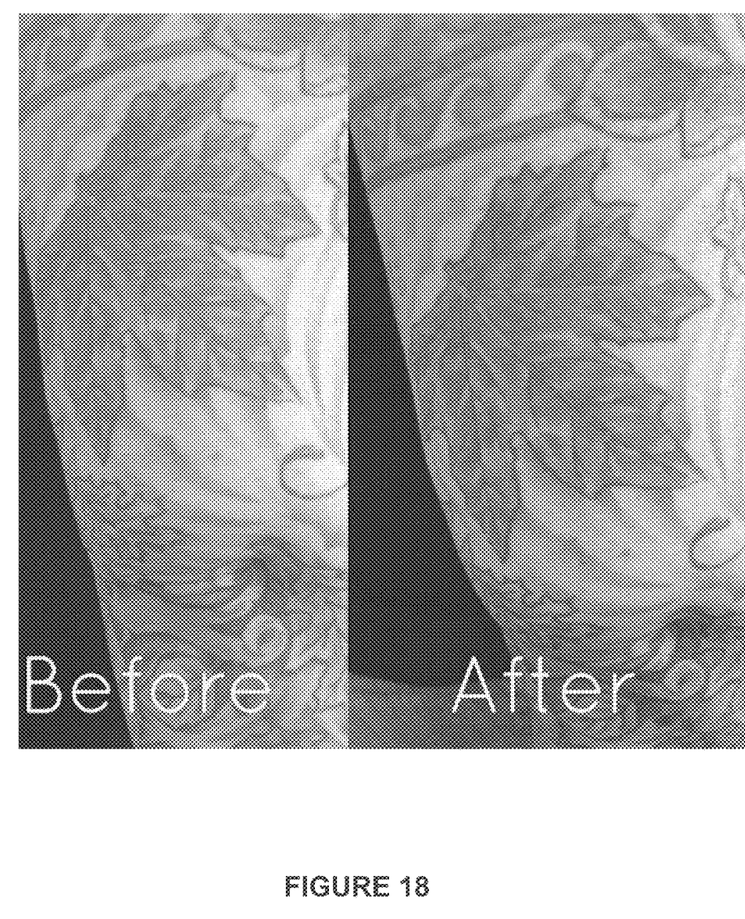
FIG. 18 is a second photograph showing colored images of a tattoo before and after use of the tattoo brightening procedure described herein.

FIG. 18 shows a second tattoo before (left image) and after (right image) application of the above procedure. In the before image the tattoo appears dull and faded; in the after image the lines are sharpened and the colors are brighter.

We claim:

1. A method for brightening tattoos or pigmented images placed below the epidermis of an individual comprising performing microdermabrasion of the surface of the epidermis of the skin over said tattoos or pigmented images by placing in contact with and moving a treatment tip having a crystalline abrasive material permanently bonded to a treatment surface thereof over said surface of the epidermis.

2. The method of claim 1 further including application of a serum to said skin surface before, during or after performing microdermabrasion of the skin surface.

3. The method of claim 2 wherein said serum comprises one or more of the group comprising Isododecane, Phenyl Trimethicone, Isostearyl Palmitate, Diethicone, oxidized corn oil, Tocopheryl Acetate (vitamin E), Glycine Soja (soybean) seed extract, Ceramides (Sphigolipids), Cyclocopentasiloxane, Dimethiconol, C12-15, Alkyl Benozoate, Olea Europea, Fruit Oil, Fragrance, Argania Spinosa Kernal Oil, Helanthus Annuus (Sunflower) Seed Oil, Passiflora Edulis Seed Oil, Copaifera Officinals (Balsam Copaiba) Resin, Chloroxylenol, Avobenzone, Octinoxate, Octisalate, Octorcrylene, Oxybenzone, Paraffin, Tocopherol, Mineral Oil, Lanolin, Dimethicone, and Beeswax.

4. A method for brightening tattoos or pigmented images formed below the epideimis of an individual comprising a. providing a device having a treatment tip for contacting the surface of the epidermis of the skin, said treatment tip having a crystalline abrasive material permanently bonded to a surface of the treatment tip, and b. bringing the crystalline abrasive material bonded to the surface of said treatment tip into contact with an area of said surface of the epiderms of the skin covering the tattoos or pigmented images while continuously moving said abrasive covered tip over said area surface of the epiderms of the skin such that the crystalline abrasive material bonded to the treatment tip removes a portion of the said surface of the epidermis of the skin over said tattoos or pigmented images.

5. The method of claim 4 wherein said device further comprises a source of vacuum and simultaneously applying said vacuum to the same area.

6. The method of claim 4 further including application of a serum to said surface before, during or after removal of said area of the surface.

7. The method of claim 6 where said device further includes structure or devices for delivering said serum.

* * * * *